(12) United States Patent  (10) Patent No.: US 7,891,356 B2
Orr et al.                  (45) Date of Patent:      Feb. 22, 2011

(54) METHOD FOR REDUCING THE EFFECTS OF GENERAL ANESTHETICS

(75) Inventors: Joseph A. Orr, Park City, UT (US); Dwayne R. Westenskow, Salt Lake City, UT (US)

(73) Assignee: Anecare Laboratories, Inc., Salt Lake City, UT (US)

( * ) Notice: Subject to any disclaimer, the term of this patent is extended or adjusted under 35 U.S.C. 154(b) by 491 days.

(21) Appl. No.: 11/843,994

(22) Filed: Aug. 23, 2007

(65) Prior Publication Data

US 2008/0041385 A1    Feb. 21, 2008

Related U.S. Application Data

(62) Division of application No. 10/680,469, filed on Oct. 7, 2003, now Pat. No. 7,353,825.

(60) Provisional application No. 60/466,934, filed on May 1, 2003.

(51) Int. Cl.
*A61M 11/00* (2006.01)

(52) U.S. Cl. .................................. 128/205.12

(58) Field of Classification Search ............ 128/205.12, 128/203.12, 200.26, 200.24; 600/529, 532, 600/538, 540, 481, 483, 500
See application file for complete search history.

(56) References Cited

U.S. PATENT DOCUMENTS

| 3,867,936 A | 2/1975 | Kelley |
| 4,360,018 A | 11/1982 | Choksi |
| 4,878,388 A | 11/1989 | Loughlin et al. |
| 5,094,235 A | 3/1992 | Westenskow et al. |
| 5,320,093 A | 6/1994 | Raemer |
| 5,471,979 A | 12/1995 | Psaros et al. |

(Continued)

FOREIGN PATENT DOCUMENTS

| EP | 0972534 A2 | 1/2000 |
| EP | 1222940 A2 | 7/2002 |

OTHER PUBLICATIONS

International Search Report of PCT/US2006/017640 dated Jan. 14, 2008 (3 pages).

(Continued)

*Primary Examiner*—Steven O Douglas
(74) *Attorney, Agent, or Firm*—Durham Jones & Pinegar, IP Law Group

(57) ABSTRACT

An apparatus for reversing inhaled anesthesia, which is configured to be positioned along a breathing circuit or anesthesia delivery circuit, includes a filter for removing one or more anesthetic agents from gases passing therethrough, as well as a component for elevating $CO_2$ levels in gases that are to be inhaled by an individual. The apparatus is configured to be positioned between a Y-connector of the breathing circuit and the portion of the breathing circuit that interfaces with the individual. The $CO_2$ level-elevating component facilitates an increase in the ventilation of the individual without resulting in a significant decrease in the individual's $P_aCO_2$ level and, thus, a decrease in the rate at which blood flows through the individual's brain. A method of reversing the effects of inhaled anesthesia includes increasing the rate of ventilation of an anesthetized individual while causing the individual to inhale gases with elevated amounts of $CO_2$ and while filtering anesthetic agents from such gases.

22 Claims, 3 Drawing Sheets

U.S. PATENT DOCUMENTS

| | | |
|---|---|---|
| 5,901,705 A | 5/1999 | Leagre |
| 6,227,196 B1 | 5/2001 | Jaffe et al. |
| 6,354,292 B1 | 3/2002 | Fisher |
| 6,536,430 B1 | 3/2003 | Smith |
| 6,564,799 B2 | 5/2003 | Fukunaga et al. |
| 6,708,689 B2 | 3/2004 | Fisher |
| 7,007,693 B2 | 3/2006 | Fuhrman et al. |
| 7,077,134 B2 | 7/2006 | Ahlmen |

OTHER PUBLICATIONS

Written Opinion of the International Searching Authority of PCT/US2006/017640 dated Jan. 14, 2008 (4 pages).

Dr. Q. Milner, Anaesthetic Breathing Systems, www.nda.ox.ac.uk/wfsa/html/u07/u07_012.htm.

International Search Report, Jul. 21, 2004 (4 pages).

Written Opinion of the International Searching Authority, Jul. 21, 2004 (6 pages).

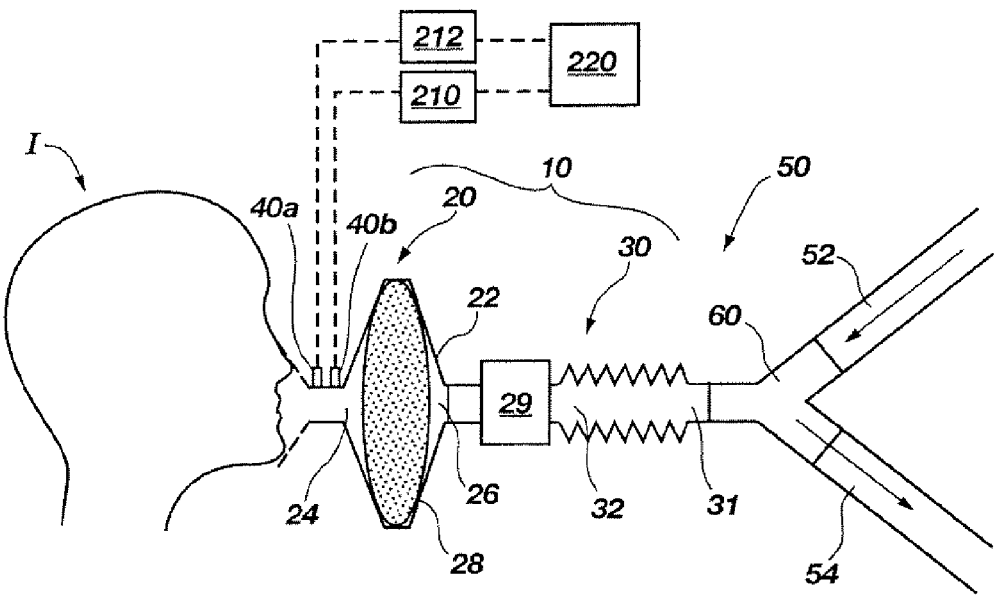
FIG. 1
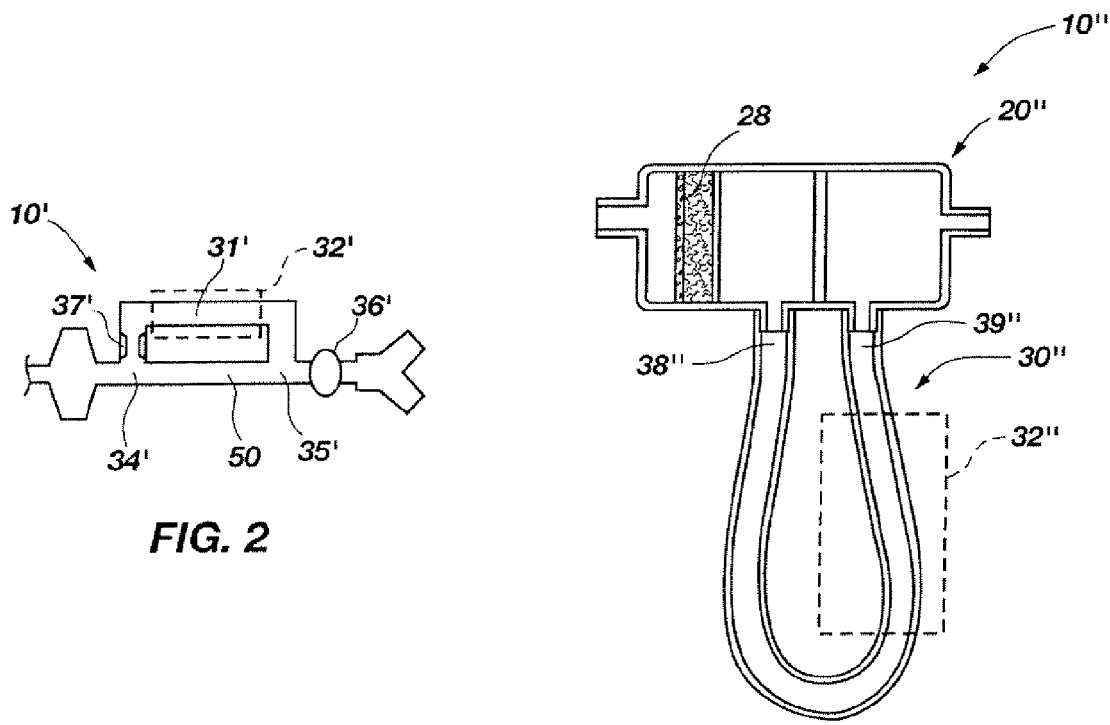
FIG. 2
FIG. 3

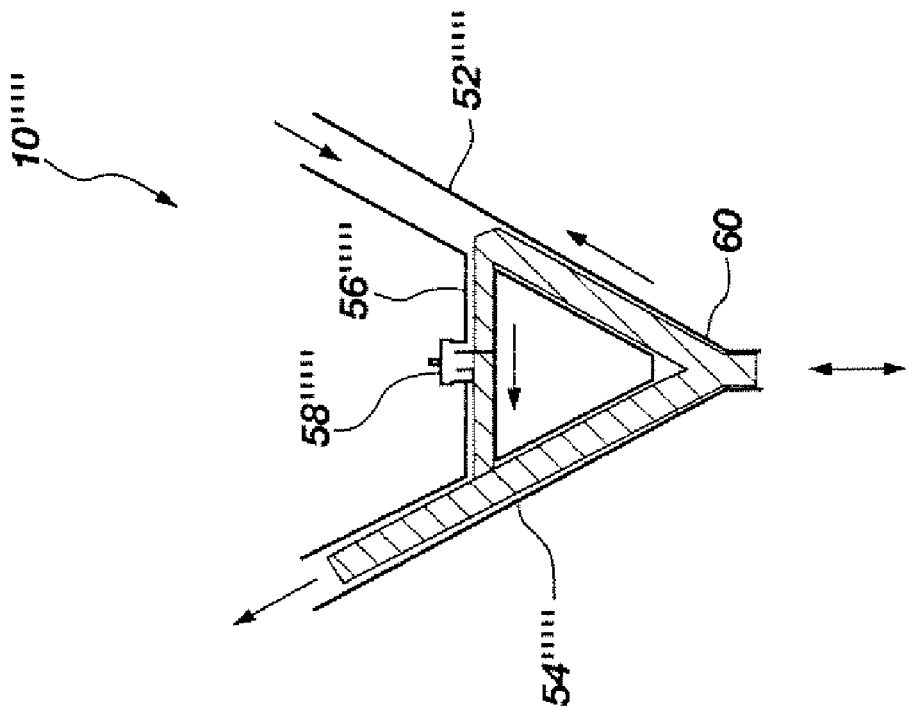
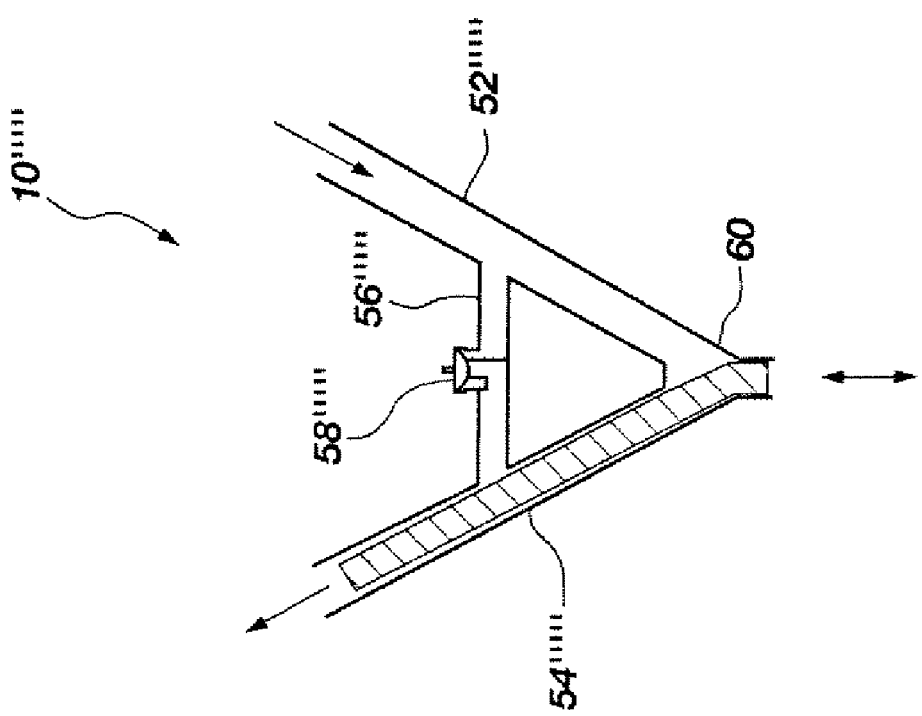

METHOD FOR REDUCING THE EFFECTS OF GENERAL ANESTHETICS

CROSS-REFERENCE TO RELATED APPLICATIONS

This application is a divisional of application Ser. No. 10/680,469, filed Oct. 7, 2003, pending, which claims the benefit of the filing date of U.S. Provisional Patent Application Ser. No. 60/466,934, filed May 1, 2003, for "Apparatus and Techniques for Reducing the Effects of General Anesthetics," pending. The disclosure of each of the previously referenced U.S. patent applications and patents is hereby incorporated by reference in its entirety.

BACKGROUND OF THE INVENTION

1. Field of the Invention

The present invention relates generally to apparatus and techniques for reversing the effects of inhaled general anesthetics. More particularly, the present invention relates to use of ventilation and rebreathing apparatus and, optionally, respiratory monitoring apparatus, in conjunction with one another to reverse the effects of inhaled general anesthetics.

2. Background of Related Art

General anesthesia is often administered to individuals as surgical procedures are being performed. Typically, an individual who is subject to general anesthesia is "hooked up" to a ventilator by way of a breathing circuit. One or more sensors may communicate with the breathing circuit to facilitate monitoring of the individual's respiration, the anesthesia, and, possibly, the individual's blood gases and blood flow. One or more anesthetic agents are typically administered to the individual through the breathing circuit.

Examples of breathing circuits that are used while anesthesia is being administered to a patient include circular breathing circuits, which are also referred to in the art as "circle systems," and Mapleson or Bain type breathing circuits, which are also referred to herein as Bain systems for the sake of simplicity.

Circle systems are typically used with adult patients. The expiratory and inspiratory limbs of a breathing circuit of a circle system communicate with one another, with a carbon dioxide remover, such as a soda lime can, being disposed therebetween. As the expiratory and inspiratory limbs communicate with one another, a circle system will typically include two or more sets of one-way valves to prevent a patient from rebreathing just-expired, $CO_2$-rich gases.

Bain systems are typically used with smaller patients (e.g., children). Bain systems include linear tubes through which both inspiratory and expiratory gases flow. Fresh gases are typically directed toward a patient interface to remove the just-expired gases therefrom before the patient can rebreathe them. As long as the fresh gas flow is higher than the flow of the patient's ventilation, there is little or no rebreathing.

When a general anesthesia is administered to an individual, respiratory or inhaled anesthetics are delivered to a patient in low concentrations, typically being diluted to a concentration of about 1% to about 5%, depending on the type of anesthetic agent used. As the individual inhales a general anesthetic agent, the anesthetic agent is carried into the lungs, where it enters the bloodstream, and is carried by the blood to various other body tissues. Once the concentration of the anesthetic reaches a sufficient level, or threshold level, in the brain, which depends upon a variety of individual-specific factors, including the size and weight of the individual, the individual becomes anesthetized. The individual remains anesthetized so long as the concentration of the anesthetic agent in the brain of the individual remains above the threshold level.

Once the procedure, typically surgery, for which the general anesthesia is given, has been completed, it is usually desirable to reverse the effects of the general anesthetic as soon as possible. Reversal of the effects of general anesthesia allows the surgical team to vacate the operating room, thereby freeing it up for subsequent surgeries and possibly reducing the cost of surgery, and also permits the anesthetist to tend to other patients, and conserves the typically expensive anesthetic agents that are used. In addition, for safety reasons, it is desirable to minimize the time an individual is under general anesthesia. Other benefits of quickly reversing anesthesia include better cognitive function for elderly patients immediately following surgery and enabling patients to protect their own airway sooner.

Reversal or discontinuation of the general anesthetic state requires that levels of the anesthetic agent in the brain decrease below the threshold level, or that the anesthetic agent be removed from the individual's brain.

It has long been known that activated charcoal and other substances can be used to selectively adsorb gaseous anesthetic agents. Accordingly, activated charcoal has found conventional use in adsorbers, such as that described in U.S. Pat. No. 5,471,979, issued to Psaros et al., that prevents anesthetic agents from escaping the breathing circuit and entering the operating room. In this regard, activated charcoal adsorbers are typically placed in the exhaust flow of the anesthesia delivery system. The potentially deleterious effects of exhaust anesthetic gases into the operating room are thereby avoided. Further, as most halocarbon anesthetics are considered to be atmospheric pollutants, the charcoals or other adsorbents of conventional anesthetic agent adsorbers prevent pollution that may be caused if gaseous anesthetic agents were otherwise released into the environment.

U.S. Pat. No. 5,094,235, issued to Westenskow et al. (hereinafter "Westenskow") describes the use of activated charcoal to hasten the removal of gaseous anesthetic agents from breathing circuits. While such a technique would be useful for preventing the reinhalation of previously exhaled anesthetic agents, more could be done to hasten the rate at which anesthetic agents are removed from the individual's brain.

Typically, the rate at which blood flows through the brain and an individual's breathing rate and breathing volume are the primary factors that determine the rate at which the levels of anesthetic agent are removed from the brain of the individual. The rate of blood flow through the brain is a determining factor because the blood carries anesthetic agents away from the brain and to the lungs. The breathing rate and breathing volume are important since they increase the rate at which anesthetic agent may be removed from the blood and transported out of the body through the lungs.

Hyperventilation has been used to increase the breath volume and/or rate of an individual and, thereby, to facilitate the removal of anesthetic agents from the individual's lungs. However, hyperventilation typically results in a reduced level of carbon dioxide ($CO_2$) in blood of the individual ($P_aCO_2$). When $P_aCO_2$ levels are decreased, the brain is less likely to signal the lungs to breathe on their own and the patient remains dependent on the ventilation from an artificial respirator. See U.S. Pat. No. 5,320,093, issued to Raemer (hereinafter "Raemer"). Additionally, the reduced $P_aCO_2$ levels that result from hyperventilation are known to cause a corresponding reduction in the rate at which blood flows through the brain, which actually decreases the rate at which the blood can carry anesthetic agents away from the brain.

Rebreathing processes, in which an individual "rebreathes" previously exhaled, $CO_2$-rich air, have been used to prevent significant decreases in $P_aCO_2$ levels during such hyperventilation. The apparatus that have been conventionally used to effect such processes, however, do not filter anesthetic agent from the exhaled air before the individual rebreathes the same. Consequently, the patient also rebreathes the previously exhaled anesthetic agent, which effectively prolongs the process of reversing the general anesthesia.

The computerized system described in Raemer was designed to overcome purported deficiencies with hyperventilation and rebreathing. The system of Raemer infuses $CO_2$ from an external source into the breathing circuit and, thus, into the individual's lungs (i.e., the $CO_2$ is not rebreathed by the individual) as general anesthesia is being reversed to speed the rate of reversal and, thus, recovery of the individual from the general anesthesia. The teachings of Raemer with respect to infusion of $CO_2$ from an external source are limited to avoidance of reintroducing anesthetic agents into the individual's brain while increasing the individual's $P_aCO_2$ to a level that will facilitate reinitiation of spontaneous breathing by his or her brain as early as possible. As the technique and system that are taught in Raemer do not include increases in the breathing rate or breathing volume of an individual, they do not accelerate the rate at which an individual recovers from anesthesia.

Accordingly, there are needs for processes and apparatus which increase the rate at which blood carries anesthetic agents from the brain, as well as the rate at which the lungs expel the anesthetic agents from the body in order to minimize the time required to reverse the levels of anesthetic agents in the brain to reverse the effects thereof.

SUMMARY OF THE INVENTION

The present invention includes methods and apparatus for accelerating the rate at which an individual recovers from general anesthesia, or for reversing the effects of anesthetic agents. These methods and apparatus maintain or increase the rate at which blood flows through the individual's brain, increase the individual's rate of respiration and respiratory volume, and prevent the individual from reinhaling previously exhaled anesthetic agents.

A method according to the present invention includes increasing the rate at which the individual inhales or the volume of gases inhaled by the individual, which may be effected with a ventilator, or respirator, while causing the individual to at least periodically breathe gases including an elevated fraction of $CO_2$. This may be effected by causing the individual to rebreathe at least some of the gases that the individual has already exhaled or by otherwise increasing the amount of $CO_2$ in gases that are to be inhaled by the individual. The rebreathed gases are filtered to at least partially remove some of the previously exhaled anesthetic agent or agents therefrom. It is currently preferred that substantially all anesthetic agents be removed from the exhaled gases prior to rebreathing thereof.

An apparatus that incorporates teachings of the present invention is configured to facilitate breathing by an individual at a rapid (i.e., above-normal) rate, while maintaining $CO_2$ levels in the individual's blood, thereby at least maintaining the rate at which blood flows to and through the individual's brain. Such an apparatus includes a filter to selectively remove anesthetic agents from gases that have been exhaled by the individual, as well a component that is configured to effect partial rebreathing by the individual, which is also referred to herein as a "rebreathing element," or another component which is configured to increase the levels of $CO_2$ inhaled by the individual. The rebreathing or other $CO_2$ level-elevating component of the apparatus facilitates an increase in the rate of ventilation of the individual, while $CO_2$ levels in blood of the individual (i.e., $P_aCO_2$) remain normal or elevated. The rebreathing or other $CO_2$ level-elevating component further allows the patient to be mechanically ventilated using a respirator at a high volume or rate while maintaining high or normal levels of $CO_2$.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which illustrate various aspects of exemplary embodiments of the present invention:

FIG. 1 is a schematic representation of an example of an anesthesia reversal system according to the present invention, including at least a portion of a breathing circuit, an element for increasing a concentration of carbon dioxide inhaled by a subject that is recovering from anesthesia, and an anesthesia filter and Y-connector positioned along the breathing circuit;

FIG. 2 schematically depicts an exemplary embodiment of the anesthesia reversal system shown in FIG. 1, which includes a rebreathing tube positioned along a breathing circuit, between the anesthesia filter and the Y-connector, which are also positioned along the breathing circuit;

FIG. 3 is a cross-sectional representation of another exemplary embodiment of the anesthesia reversal system of FIG. 1, in which a rebreathing tube which extends from and back to the anesthesia filter;

FIGS. 6A and 6B are schematic depictions of yet another embodiment of anesthesia reversal system of the present invention, in which one or more conduits and valves are positioned between inspiratory and expiratory limbs that branch off of the Y-connectors;

DETAILED DESCRIPTION

Figure 4:
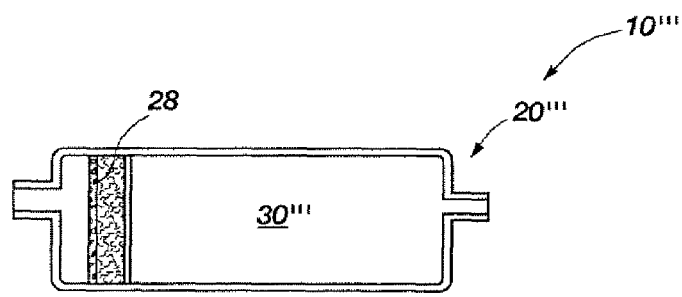
FIG. 4 is a cross-sectional representation of another embodiment of anesthesia reversal system of the present invention, in which the anesthesia filter thereof includes an additional deadspace volume which is configured to effect rebreathing.

With reference to the FIG. 1, an anesthesia reversal system 10 according to the present invention, which may be positioned along a portion of a breathing circuit 50, between an individual I and a Y-connector 60, and includes a filter 20 and a rebreathing component 30. An inspiratory limb 52 and an expiratory limb 54 may be coupled to Y-connector 60 and, thus, to breathing circuit 50. Notably, the inspiratory and expiratory limbs of some breathing circuits are coaxial. Nonetheless, the junction between the inspiratory and expiratory hoses of such breathing circuits is still referred to as a "Y-connector."

As depicted, filter 20 is positioned near the endotracheal tube for an intubated patient or over the mouth and/or nose of an individual I when breathing through a mask or mouthpiece so as to remove exhaled anesthetic agents before they flow into the remainder of anesthesia reversal system 10, where they might otherwise be adsorbed by the surfaces of anesthesia reversal system 10 to remove inhalation anesthetics and be subsequently inhaled by the individual. Of course, placement of filter 20 at alternative locations of anesthesia reversal system 10 is also within the scope of the present invention, so long as filter 20 is positioned between the individual I and rebreathing component 30.

Filter 20 may include a housing 22 with a proximal (relative to individual I) port 24 and a distal port 26, which, in the depicted example, are on opposite sides of filter 20. In addition, an anesthesia filter member 28 is contained within housing 22, in communication with both proximal port 24 and distal port 26.

Proximal port 24 and distal port 26 may both be configured for connection to standard breathing circuit fittings. For example, proximal port 24 and distal port 26 may be configured to connect to standard 15 mm or 22 mm respiratory fittings. As such, once reversal of general anesthesia or other inhaled anesthesia is desired, filter 20 may be positioned along a breathing circuit 50 which is already in communication with an airway (i.e., the mouth or nose, trachea, and lungs) of individual I.

Anesthesia filter member 28 may comprise any type of filter which is known to selectively adsorb one or more types of anesthetic agents. By way of example and not to limit the scope of the present invention, anesthesia filter member 28 may comprise an activated charcoal, or activated carbon, filter, a crystalline silica molecular sieve, a lipid-based absorber (e.g., which operates in accordance with the teachings of U.S. Pat. No. 4,878,388 to Loughlin et al., the disclosure of which is hereby incorporated herein in its entirety by this reference), a condensation-type filter, or any other type of filtering mechanism which captures or otherwise removes anesthetic vapors from the gases that have been exhaled by individual I. If filter member 28 comprises a particulate material, such as activated charcoal or crystalline silica, the particulate material may be contained by a porous member, a screen, or the like.

As anesthesia filter member 28 communicates with both proximal port 24 and distal port 26, it will remove anesthetic agents from gases that are inhaled by individual I, as well as from gases that are exhaled by individual I.

Optionally, filter 20 may also include an antimicrobial filter member 29 of a type known in the art, such as 3M FILTRETE® filter media or other electrostatic polypropylene fiber based filter media. Like anesthesia filter member 28, antimicrobial filter member 29 communicates with breathing circuit 50 (e.g., by way of proximal port 24 and distal port 26 of filter 20). Accordingly, antimicrobial filter member 29 is positioned to receive substantially all of the gases that are inhaled and exhaled by individual I and, thus, to remove bacteria, viruses, or other pathogens from those gases. Of course, anesthesia reversal systems that include antimicrobial filters that are separate from filter 20 are also within the scope of the present invention.

As shown in FIG. 1, filter 20 and rebreathing component 30 are in direct communication with one another. As will be shown in greater detail hereinafter, rebreathing component 30 may actually be a part of filter 20, rather than separate therefrom.

Rebreathing component 30 may be configured to provide a volume or an amount of deadspace which will maintain a particular level of $CO_2$ in the blood (i.e., $P_aCO_2$) of individual I. In the depicted example, rebreathing component 30 comprises conduit 31 including a section 32 of expandable tubing that can be extended to increase or compressed to decrease the amount of deadspace for containing previously exhaled gases which are to be rebreathed by individual I. Of course, other types of rebreathing apparatus, such as one of those (excepting the tracheal gas insufflation device) described in U.S. Pat. No. 6,227,196, issued to Orr et al., the disclosure of which is hereby incorporated herein in its entirety by this reference, or any other known type of partial rebreathing apparatus, may be used in anesthesia reversal system 10 as rebreathing component 30.

It is also within the scope of the present invention to include another element, such as a respiratory flow sensor or gas sampling port 40a therefor, or a capnometer or gas sampling port 40b therefor, as known in the art, at any position along an anesthesia reversal system 10 according to the present invention (e.g., close to individual I, between filter 20 and rebreathing component 30, close to Y-connector 60, etc.). For example, when gas sampling ports 40a, 40b are used, they may be of conventional configuration (e.g., for facilitating gas sampling at a rate of about 50 ml/min to about 250 ml/min), such as fittings that are configured to be disposed at an end or along the length of breathing circuit 50 or an inspiratory or expiratory limb 52, 54 in communication therewith.

Turning now to FIGS. 2 through 6, specific examples of anesthesia reversal systems that incorporate teachings of the present invention are shown.

The embodiment of anesthesia reversal system 10' shown in FIG. 2 includes a rebreathing component 30' that comprises a section of rebreathing conduit 31', which communicates with breathing circuit 50 at two locations 34' and 35' between filter 20 and Y-connector 60. Rebreathing conduit 31' may include a section 32' which is volume-adjustable in a manner known in the art (e.g., by way of corrugations, etc.). One or more valves 36', flow restrictors 37', or a combination thereof may be positioned along breathing circuit 50 or rebreathing conduit 31' to control the flow of gases into and out of conduit 31'.

Another embodiment of anesthesia reversal system 10", which is shown in FIG. 3, includes a rebreathing component 30" that communicates directly with a filter 20" rather than with breathing circuit 50. As shown, rebreathing component 30" may be configured as a loop of conduit 31". One or both ends 38" and 39" of conduit 31" may communicate with filter 20" at a location which is on the distal side of anesthesia filter member 28 relative to the location of individual I (FIG. 1) (e.g., between anesthesia filter member 28 and distal port 26) such that gases are filtered before and/or after passage thereof through conduit 31". Like rebreathing component 30' (FIG. 2), rebreathing component 30" may include a volume-adjustable section 32".

FIG. 4 depicts another embodiment of anesthesia reversal system 10''', in which filter 20" figured to provide a deadspace volume 30''' in which at least some carbon dioxide rich gases are collected as individual I exhales. As shown, deadspace volume 30''' is located on the distal side of anesthesia filter member 2S, such that the exhaled gases that have collected therein are filtered as they flow therein and, later, as they are drawn therefrom (e.g., as individual I (FIG. 1) subsequently inhales).

Figure 5:
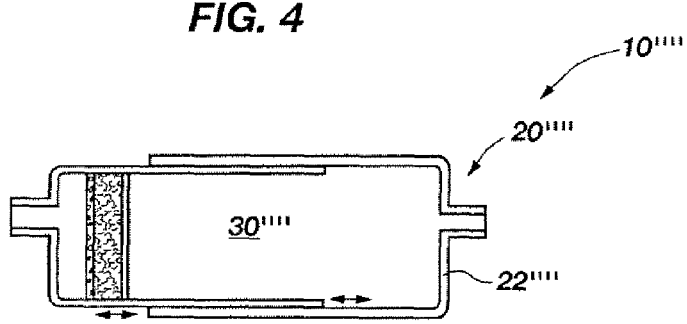
FIG. 5 is a cross-sectional representation of still another embodiment of anesthesia reversal system that incorporates teachings of the present invention, in which the anesthesia filter includes a volume-adjustable deadspace to effect rebreathing.

Yet another embodiment of anesthesia reversal system 10'''' that incorporates teachings of the present invention is pictured in FIG. 5. Anesthesia reversal system 10'''' is much like anesthesia reversal system 10''', which is shown in and described with reference to FIG. 4. The primary difference between anesthesia reversal system 10'''' and anesthesia reversal system 10''' is that the deadspace volume 30'''' of anesthesia reversal system 10'''', which is at least partially defined by body 22'''' of filter 20'''', is adjustable, for example, by enlarging or reducing the amount of space occupied by body 22'''' (e.g., by the illustrated sliding motion or as otherwise will be readily apparent to those of ordinary skill in the art.

As another alternative, pictured in FIGS. 6A and 6B, an anesthesia reversal system 10''''' of the present invention may include one or more shunt lines 56''''' positioned between an inspiratory limb 52''''' and an expiratory limb 54''''' to provide a selectively sized deadspace in the circuit. In this embodiment, inspiratory limb 52''''' and expiratory limb 54''''' act as part of the deadspace. A two-way shunt valve 58''''' is positioned along each shunt line 56''''' to selectively direct the flow of inspired and expired gas.

During normal or baseline breathing, as depicted in FIG. 6A, the two-way shunt valve 58''''' will be in a closed position and exhaled gases, which are represented by the shaded area, will enter the expiratory limb 54'''''.

In order to facilitate rebreathing, as pictured in FIG. 6B, two-way shunt valve 58''''' is opened, permitting exhaled gases to fill a portion of inspiratory limb 52''''', substantially all of expiratory limb 54''''' and shunt line 56''''', all of which serve as deadspace.

The deadspace may be rendered adjustably expandable by using an expandable conduit for all or part of one or more of inspiratory limb 52''''', expiratory limb 54''''', and shunt line 56'''''.

Figure 7:
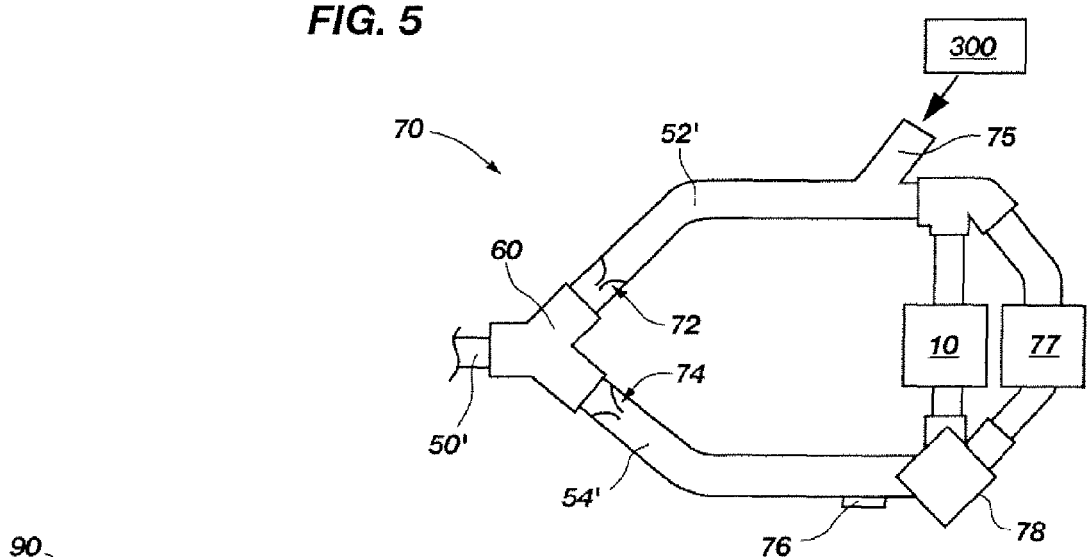
FIG. 7 schematically depicts use of an anesthesia reversal system according to the present invention along a conventional circular system.
Figure 8:
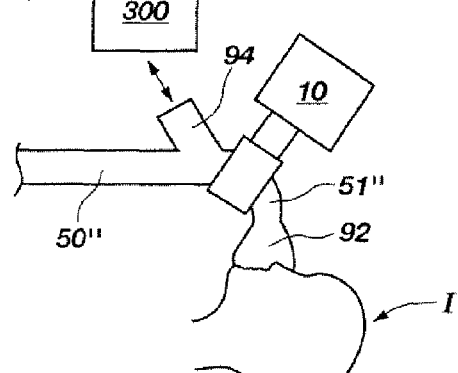
FIG. 8 schematically illustrates use of an anesthesia reversal system of the present invention with a conventional Bain system.

Turning now to FIGS. 7 and 8, use of an anesthesia reversal system 10 of the present invention in combination with various anesthesia delivery systems is shown.

In FIG. 7, a circle system 70 is illustrated. Circle system 70, which includes an interconnected (e.g., in the configuration of a circle, or loop) inspiratory limb 52' and expiratory limb 54'. Inspiratory limb 52' and expiratory limb 54' are coupled to a Y-connector 60 which, in turn, is coupled to a breathing circuit 50'. Breathing circuit 50' is configured to interface with an individual I (FIG. 1) in a known manner (e.g., by intubation, with a mask, with a nasal cannula, etc.). Circle system 70 also includes at least two one-way valves 72 and 74, which are positioned across inspiratory limb 52' and expiratory limb 54', respectively, at opposite sides of Y-connector 60. One way valves 72 and 74 restrict the flow of gases through circle system 70 to a single direction, such that expired gases are prevented from flowing directly into inspiratory limb 52' and to prevent individual I from inhaling gases directly from expiratory limb 54'.

Inspiratory limb 52' of circle system 70 includes at least one gas inlet 75, such as a port that facilitates coupling to an anesthesia delivery system 300, a mechanical ventilator, or a breathing bag, or which permits air from an environment external to circle system 70 (e.g., an operating room, a patient room in a hospital, etc.) to flow therein. An expiratory element 76, such as an expiratory spill valve of a known type is positioned along expiratory limb 54' of circle system 70.

As shown, expiratory limb 54' and expiratory limb 52' are joined at a location which is distal relative to Y-connector 60 and individual I by a carbon dioxide removal element 77, such as a soda lime canister. As one-way valve 72 prevents exhaled gases entering inspiratory limb 52', the exhaled gases are directed through expiratory limb 54' and, depending upon the positioning of a bypass valve 78 positioned along expiratory limb 54', possibly into carbon dioxide removal element 77, which reduces the amount of carbon dioxide present in such gases.

Additionally, circle system 70 includes an anesthesia reversal system 10. As shown, anesthesia reversal system 10 selectively communicates, by way of bypass valve 78, with expiratory limb 54' of circle system 70 and is positioned in parallel to carbon dioxide removal element 77. The volume of deadspace that may be present within circle system 70 depends upon whether or not expiratory element 76 causes exhaled gases to remain within expiratory limb 54' and upon whether bypass valve 78 is positioned to permit exhaled gases to bypass carbon dioxide removal element 77. In addition, when a mechanical ventilator is coupled to gas inlet 75, the volume of deadspace within circle system 70 depends upon the proximity of the gas inlet 75 to a junction 80 of anesthesia reversal system 10 with inspiratory limb 52'.

If expiratory element 76 is at least partially closed, depending upon the positioning of bypass valve 78, at least some of the gases that have been exhaled by individual I and which are flowing through expiratory limb 54' Nay be diverted from carbon dioxide removal element 77 into anesthesia reversal system 10. If bypass valve 78 is adjustable to more than two positions, exhaled gases may be directed into both anesthesia reversal system 10 and carbon dioxide removal element 77. Thus, it may be possible to carefully regulate the amounts of exhaled gases that are directed into anesthesia reversal system 10 and carbon dioxide removal element 77, providing control over the amount of carbon dioxide that is rebreathed by individual I. Further, if bypass valve 78 is positioned such that the previously exhaled gases flow through anesthesia reversal system 10, the amount of carbon dioxide that remains in gases that pass through anesthesia reversal system 10 will be relatively high, while the amount of anesthesia present in such gases will be reduced by filter 20.

Then, when individual I inhales or is caused to inhale, at least a portion of the gases that are inhaled (i.e., the gases that remain within breathing circuit 50' and anesthesia reversal system 10) will be previously exhaled, $CO_2$-rich gases.

As circle system 70 may itself serve as a deadspace from which an individual I may be caused to rebreathe previously exhaled, carbon dioxide rich gases, an anesthesia reversal system 10 that is used in a circle system 70 may lack additional deadspace, such as a rebreathing component 30.

Referring now to FIG. 8, a Bain system 90 that incorporates teachings of the present invention is depicted. Bain system 90 includes a linear breathing circuit 50'', a patient interface 92 located at one end 51'' of breathing circuit 50'' and a fresh gas inlet 94, which is configured to communicate with an anesthesia delivery system 300 of a known type, a mechanical ventilator, a breathing bag, or the environment external to Bain system 90, positioned along the length of breathing circuit 50''. In addition, Bain system 90 includes an anesthesia reversal system 10 that communicates with breathing circuit 50''. Anesthesia reversal system 10 is preferably positioned proximate to patient interface 92 so as to optimize the amount of anesthesia removed from the exhaled gases and, thus, minimize the amount of anesthetic agent rebreathed by an individual I as the affects of the anesthesia are being reversed.

While FIGS. 2 through 8 illustrate various systems that are useful for providing a deadspace volume from which an individual I may rebreathe as individual I is being withdrawn from anesthesia, any other method, apparatus, or system that induces rebreathing of carbon dioxide in a mechanical breathing circuit for the purpose of reversing the affects of anesthesia on an individual are also within the scope of the present invention.

Figure 9:
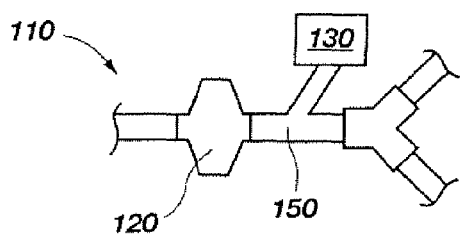
FIG. 9 is a schematic representation of yet another embodiment of anesthesia reversal system of the type shown in FIG. 1, in which the element that increases a concentration of carbon dioxide inhaled by the subject comprises a carbon dioxide infuser.

Turning now to FIG. 9, an anesthesia reversal system 110 that includes a carbon dioxide infusion element 130 rather than a rebreathing component is depicted. As illustrated, carbon dioxide infusion element 130 communicates with a breathing conduit 150. A filter 120 of anesthesia reversal system 110 is also positioned along breathing conduit 150, proximate to individual I (FIG. 1), so as to reduce the amount of anesthesia in gases that are exhaled by individual I and, thus, to minimize the amount of anesthesia that remains in any gases that are withdrawn from breathing conduit 150 and rebreathed by individual I.

With returned reference to FIG. 1 (although anesthesia reversal system 110 shown in an described with reference to FIG. 9 may be used in a similar manner), anesthesia reversal system 10 may be used by placing the same in communication with a breathing circuit or anesthesia delivery circuit (e.g., those shown in FIGS. 7 and 8). It is currently preferred that filter 20 be positioned proximate to individual I and that rebreathing component 30 be positioned closer to Y-connector 60. In the case of anesthesia recovery system 110 (FIG. 9), the position of carbon dioxide infusion element 130 relative to that of filter 120 is irrelevant.

A deadspace (e.g., in the form of the volume within a rebreathing component 30) may be adjusted by an anesthetist to provide the desired volume of deadspace therein in order to facilitate rebreathing. For example, when the deadspace volume is at least partially located within corrugated tubing, the deadspace volume may be adjusted by extending or contracting the length of the corrugated tubing. As another example, when a fixed volume of deadspace is present, or even with a volume-adjustable deadspace, the amount of carbon dioxide within the deadspace may be tailored by adjusting the flow of "fesh" gases, including recycled gas from which carbon dioxide has been removed. When the flow of "fresh" gases is lower than the flow of individual I's ventilation, rebreathing of gases within the deadspace may occur.

Once anesthesia reversal system 10 has been positioned in communication with a breathing circuit or anesthesia delivery system, gases that are exhaled by individual I pass into and through filter 20, which removes at least some anesthetic agents from the exhaled gases. At least a portion of the volume of the filtered, exhaled gases enters and at least temporarily remains within the deadspace (e.g., rebreathing component 30). Also, by reducing levels of anesthetic agents in gases that are exhaled by individual I, filter 20 may effectively reduce levels of anesthetic agents that escape into the environment (e.g., the operating room, recovery room, atmosphere, etc.) when individual I exhales.

When individual I inhales, at least a portion of the inhaled gases are drawn from the deadspace (e.g., from rebreathing component 30), with any other gases being drawn from either the air or from a source of inspiratory gases that communicate with a ventilator. As the inhaled gases are drawn through breathing circuit 50, they pass through filter 20, where at least some of the remaining anesthetic agents therein are removed therefrom. Notably, in most anesthesia systems, very high concentrations of oxygen (>90%) are used. Thus, individual I may rebreathe the same gas many times and still be sufficiently oxygenated.

It is currently preferred that partial rebreathing processes (i.e., only a portion of the gases inhaled by the patient were previously exhaled, while the other portion of gases are "fresh") be used in reversing the effects of inhaled anesthesia. This is because individual I requires some oxygen during the reversal. Of course, the use of total rebreathing processes is also within the scope of the invention. The manner in which rebreathing is effected may be varied or controlled to provide the desired affects, while providing individual I with sufficient oxygen.

Of course, a gas sensor and monitor 210 (e.g., an anesthetic gas monitor of a known type) that measures carbon dioxide or oxygen may be used to monitor the ventilatory gases of individual I. A respiratory flow sensor and monitor 212 may also be used to monitor the flow of ventilation of individual I. Gas concentrations may be determined by a processing element 220 (e.g., a computer processor or controller, a smaller group of logic circuits, etc.) that communicates with gas sensor and monitor 210 and flow sensor and monitor 212, as known in the art. If the carbon dioxide or oxygen levels (e.g., blood gas content, respiratory fraction, etc.) reach undesirable levels, adjustments may be made to the deadspace volume (e.g., within rebreathing component 30), or volume of rebreathed gases, to the concentration of oxygen or carbon dioxide in the other inhaled gases, or to any combination of the foregoing. Such adjustment may be made automatically, such as by processing element 220, which, of course, operates under control of appropriate programming and communicates with one or more of a ventilator and valves (e.g., bypass valve 78 (FIG. 7)) of the anesthesia reversal system 10. Alternatively, adjustment of the deadspace may be effected semiautomatically, such as in accordance with instructions provided by a processing element, or manually.

By combining a filter 20 and an element for increasing the amount of carbon dioxide inhaled by individual I (e.g., with a rebreathing component 30 or carbon dioxide infusion element 130) in an anesthesia reversal apparatus of the present invention, ventilation of an individual I may be increased while maintaining normal to high $P_aCO_2$ levels, which maintains or increases blood flow levels and, thus, the rate at which anesthetic agents may be removed from the brain as the increased ventilation improves the rate at which anesthetic agents are removed from the blood and, thus, exhaled by individual I.

While much of the description provided herein focuses on the reversal of general anesthesia, it should be appreciated that the apparatus and methods of the present invention are useful for reversing the effects of any type of inhaled anesthesia, whether or not such inhaled anesthetic agents have a general anesthetic effect.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A method employing at least one apparatus for facilitating emergence of a subject from inhaled anesthesia, the method comprising:
    decreasing a concentration of anesthetic agents in blood flowing into the brain of the subject with at least one apparatus for facilitating emergence of a subject from inhaled anesthesia;
    increasing blood flow to the brain of the subject with the at least one apparatus; and
    preventing the subject from inhaling previously exhaled anesthetic agents with the at least one apparatus.

2. The method of claim 1, wherein increasing blood flow to the brain comprises:
controlling an amount of carbon dioxide inhaled by the subject.

3. The method of claim 2, wherein controlling comprises causing the subject to inhale air or a gas mixture with a fixed concentration of carbon dioxide.

4. The method of claim 2, wherein controlling comprises causing the subject to inhale air or a gas mixture with an above normal amount of carbon dioxide.

5. The method of claim 4, wherein controlling comprises causing the subject to rebreathe previously exhaled gases.

6. The method of claim 5, wherein causing comprises adjusting a volume of the previously exhaled gases or an amount of carbon dioxide in the previously exhaled gases.

7. The method of claim 6, wherein adjusting comprises permitting a portion of the previously exhaled gases to escape a volume from which causing is to be effected, removing carbon dioxide from a portion of the previously exhaled gases, or controlling a flow rate of fresh gases into a volume from which causing is to be effected.

8. The method of claim 5, wherein preventing comprises removing at least some anesthetic agents from the previously exhaled gases.

9. The method of claim 8, wherein removing comprises removing substantially all anesthetic agents from the previously exhaled gases.

10. The method of claim 4, wherein causing comprises causing the subject to inhale air or a gas mixture which is substantially free of anesthetic agents.

11. The method of claim 1, further comprising:
preventing the subject from inhaling pathogens.

12. A method employing at least one apparatus for facilitating emergence of a subject from inhaled anesthesia, the method comprising:
increasing ventilation of the subject relative to the subject's ventilation under anesthesia with a ventilator;
causing the subject to inhale gases including an increased amount of carbon dioxide, including at least an atmospheric amount of carbon dioxide, relative to an amount of carbon dioxide inhaled by the subject under anesthesia, with a $CO_2$ level-elevating component; and
preventing the subject from inhaling previously exhaled anesthetic agents with an anesthesia removal component.

13. The method of claim 12, wherein causing comprises controlling an amount of carbon dioxide inhaled by the subject with the $CO_2$ level-elevating component.

14. The method of claim 13, wherein controlling comprises causing the subject to inhale air or a gas mixture with a fixed concentration of carbon dioxide with the $CO_2$ level-elevating component.

15. The method of claim 13, wherein controlling comprises causing the subject to inhale air or a gas mixture with an above atmospheric amount of carbon dioxide with the $CO_2$ level-elevating component.

16. The method of claim 15, wherein controlling comprises causing the subject to rebreathe previously exhaled gases with a rebreathing element.

17. The method of claim 16, wherein causing comprises adjusting a volume of the previously exhaled gases or an amount of carbon dioxide in the previously exhaled gases.

18. The method of claim 17, wherein adjusting comprises permitting a portion of the previously exhaled gases to escape a volume of the rebreathing element from which causing is to be effected, removing carbon dioxide from a portion of the previously exhaled gases with a $CO_2$ removal component, or controlling a flow rate of fresh gases into a volume of the rebreathing element from which causing is to be effected.

19. The method of claim 16, wherein preventing comprises using the anesthesia removal component to remove at least some anesthetic agents from the previously exhaled gases.

20. The method of claim 19, wherein removing comprises using the anesthesia removal component to remove substantially all anesthetic agents from the previously exhaled gases.

21. The method of claim 15, wherein causing the subject to inhale air or a gas mixture with an above normal amount of carbon dioxide comprises the subject to inhale air or a gas mixture which is substantially free of anesthetic agents.

22. The method of claim 12, further comprising:
preventing the subject from inhaling pathogens with a pathogen removal component.

* * * * *